United States Patent
Leschinsky et al.

(12) 
(10) Patent No.: US 6,179,825 B1
(45) Date of Patent: Jan. 30, 2001

(54) OVAL VASCULAR CATHETER

(75) Inventors: Boris Leschinsky, Waldwick; Dennis Goupil, Montville, both of NJ (US)

(73) Assignee: Datascope Investment Corp., Montvale, NJ (US)

( * ) Notice: Under 35 U.S.C. 154(b), the term of this patent shall be extended for 0 days.

(21) Appl. No.: 08/818,120

(22) Filed: Mar. 15, 1997

(51) Int. Cl.⁷ .................................................. A61M 31/00
(52) U.S. Cl. ............................ 604/509; 604/96; 604/507
(58) Field of Search ........................... 606/191, 192–194, 606/198; 604/101, 528, 158, 507, 93.01, 96.01, 104, 509, 105, 106, 107, 108, 500

(56) References Cited

U.S. PATENT DOCUMENTS

| | | | |
|---|---|---|---|
| 5,447,503 | * | 9/1995 | Miller ..................................... 604/280 |
| 5,620,417 | * | 4/1997 | Jang et al. ............................... 604/96 |
| 5,743,875 | * | 4/1998 | Sirhan et al. ........................... 604/96 |

* cited by examiner

*Primary Examiner*—Manuel Mendez
(74) *Attorney, Agent, or Firm*—J. Gary Mohr

(57) ABSTRACT

An apparatus and method for insertion of a catheter, such as an IAB catheter, into a blood vessel such that the cross-sectional area of the catheter will be minimized while the circumference of the catheter is maximized. The apparatus is formed as an oval tube of flexible plastic. When placed in a blood vessel, the catheter retains its oval configuration to minimize obstruction to blood flow. During inflation of the balloon bladder at the end of the catheter, the catheter retains its general oval shape. When the catheter is placed in the blood vessel by pre-loading the catheter over a guide wire and inserting the catheter and guide wire without an introducer sheath into the blood vessel both the catheter and its leading balloon bladder are approximately of the same perimeter thereby reducing the possibility of arterial bleeding.

3 Claims, 5 Drawing Sheets

CURRENT PROFILES (PRIOR ART)

NON-CIRCULAR PROTOTYPES

OVAL VASCULAR CATHETER

BACKGROUND OF THE INVENTION

1. Field of the Invention

The present invention relates generally to catheters inserted into the vascular system for extended periods of time, and more particularly, to an oval IAB catheter for insertion into a blood vessel, and the method for placing such catheter into the blood vessel.

2. Description of the Related Art

Insertion of catheters into the vascular system of humans is a commonly performed procedure. These catheters function as a conduit for inflation of IAB. When a catheter needs to be in place for an extended period of time, it is common to place the catheters from the lower half of the body. Such catheters may have single or multiple lumens, and are typically made from a relatively rigid plastic material with a standard, round cross-section, both to facilitate placement of the catheter into the vessel and to prevent the catheter lumens from collapsing within the vessel. Generally speaking theses catheters are constructed in such a way that the lumen or lumens extending therethrough retain their circular cross-sectional configuration unless an external mechanical force compresses the catheter.

A complication of placing such a catheter is formation of clots on the wall of the catheter located in the vascular system. Blood clots form for several reasons. The vessel causes turbulence and slowing of the blood flow through the vessel, and these factors induce the formation of clots. Generally, the greater the cross-sectional area of the catheter relative to the blood vessel, the greater the induced turbulence and slowing of the blood. In addition, the catheter is a foreign body, and the surface of the catheter in contact with blood is an ideal site for clot formation. Once again, the greater the amount of surface area of the catheter or other foreign body in contact with the blood, the more likely that clots will form.

Such clots can break away and flow in the blood stream to the heart and lungs, causing severe complications. Furthermore, the formation of clots can often cause such vessels to become irreversibly damaged and thrombose, preventing further blood flow through such vessels. This may ultimately cause debilitating swelling of the limb.

Accordingly, it is an object of the present invention to provide a catheter which reduces the likelihood of the formation of clots or reduction in blood flow within the blood vessel into which the catheter is placed while reducing the chances of arterial bleeding at the puncture site of the artery all due to its oval or non-circular shape which has approximately the same perimeter as the balloon attached to the oval catheter.

It is another object of the present invention to provide such a catheter which presents a minimal cross-section obstruction to the normal flow of blood within the blood vessel, yet has a maximum circumference to prevent blood leakage at the point of insertion. However, while it is desirable to have a catheter that has a low profile shape, when such a catheter is inserted behind the balloon bladder attached to the front of the catheter, which bladder is larger than the normally used circular catheter, the bleeding may occur at the site of introduction into the body. This is due to the fact the larger diameter of the wrapped balloon bladder which first enters the insertion site leaves behind a diameter opening larger than the smaller circular catheter following the balloon into the insertion site and thereby leaving a space for blood to flow from said opening. Such a problem is discussed, especially when sheathless insertion is performed, in U.S. Pat. No. 4,897,077. The solution to the blood leakage, in that Patent, was to use a hemostasis sheath, but that doesn't solve the problem of the catheters obstruction of blood flow in the blood vessel.

A still further object of the present invention is to provide a method for conveniently placing such a catheter within the desired blood vessel using commonly available vascular apparatus.

These and other objects of the present invention will become more apparent to those skilled in the art as the description of the present invention proceeds.

SUMMARY OF THE INVENTION

Briefly described, and in accordance with the preferred embodiments thereof, the present invention is a catheter apparatus for inserting an IAB device into the body in a modified percutaneous insertion technique without the use of an insertion sheath. Additionally, there is described a device and method to control bleed back through the insertion site after insertion of the wrapped balloon bladder.

In accordance with the invention, an insertion technique is provided to enable insertion of an wrapped balloon bladder followed by an oval catheter device directly into a blood vessel over a guide wire, without the need first to inset and use an introducer sheath and with the catheter having a profile within the blood vessel such that it minimizes blood flow restriction.

DESCRIPTION OF THE DRAWINGS

The invention will now be described with reference to the following drawings, which are merely exemplary and are not meant to limit the scope of the invention in any respects.

DESCRIPTION OF THE PREFERRED EMBODIMENT

Figure 1A:
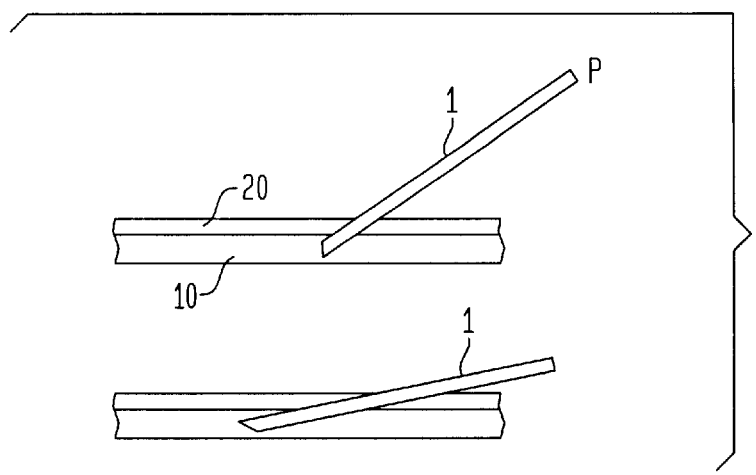
FIGS. 1a–d show in succession (a) the puncture of the skin and artery, (b) insertion of the guide wire, (c) dilation of the insertion site and (d) insertion of an insertion sheath all employing a prior art (Seldinger) technique.
Figure 1B:
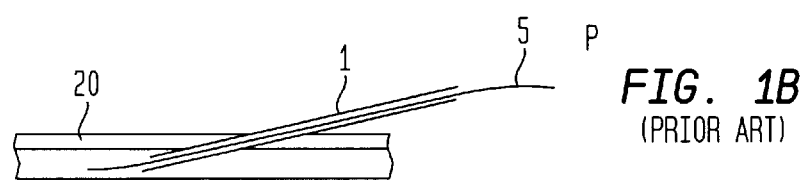
Figure 1C:
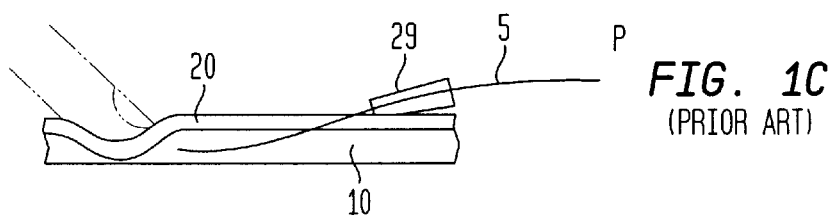
Figure 1D:
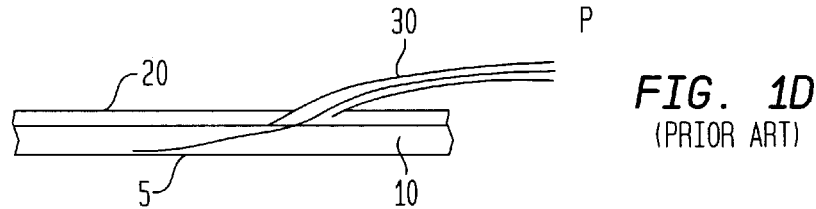
Figure 4:
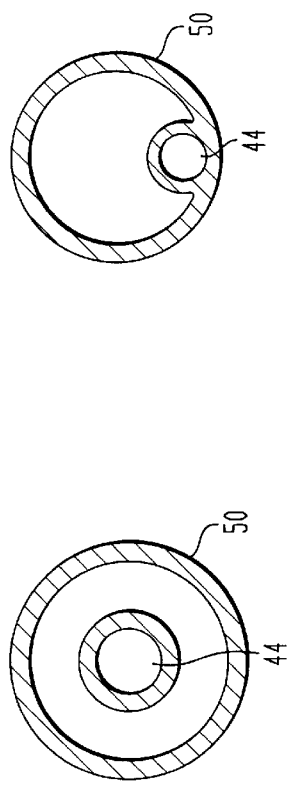
FIG. 4 is a sampling of oval or non-circular cross-sectional area catheters that may be used in the present invention as compared to the present prior art profiles of catheters.
Figure 4:
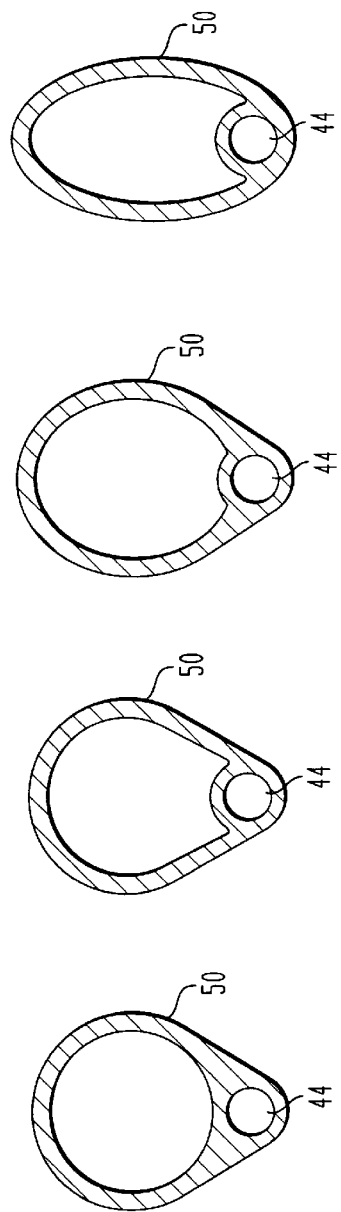
Figure 5:
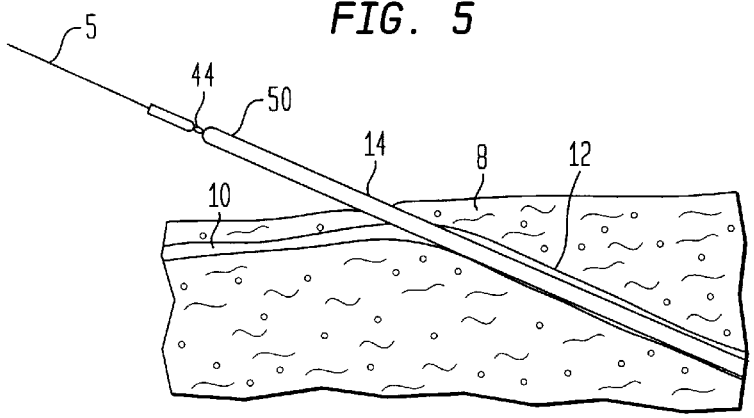
FIG. 5 is a side elevation view of an IAB device showing the oval catheter of approximately the same cross-sectional area as the puncture site accordance with the present invention directly inserted into the femoral common artery without an insertion sheath.

FIGS. 1a–d. shows various steps employed in the prior art (Seldinger) technique for inserting an IAB device percutaneously. There is show needle 1, guide wire 5, dilator 29, insertion sheath 30, skin 20 and femoral artery 10. FIG. a shows puncture of the skin and the femoral artery using a hypodermic needle 1. FIG. 1b shows placement of a guide wire 5 into the artery through the hollow bore of the needle. FIG. 1c shows removal of the hypodermic needle 1 from the artery leaving the guide wire 5 in place and the dilation of the opening with dilator 29 (e.g., Grunzig type). Finally, FIG. 1d shows placement of any insertion sheath 30, normally used to control arterial bleeding at the puncture site, into the artery over the guide wire following dilation of the insertion site. This sheath 30, however, is not needed in the present invention due to the oval cross-section area of catheter 50 as shown in FIG. 4.

Figure 2:
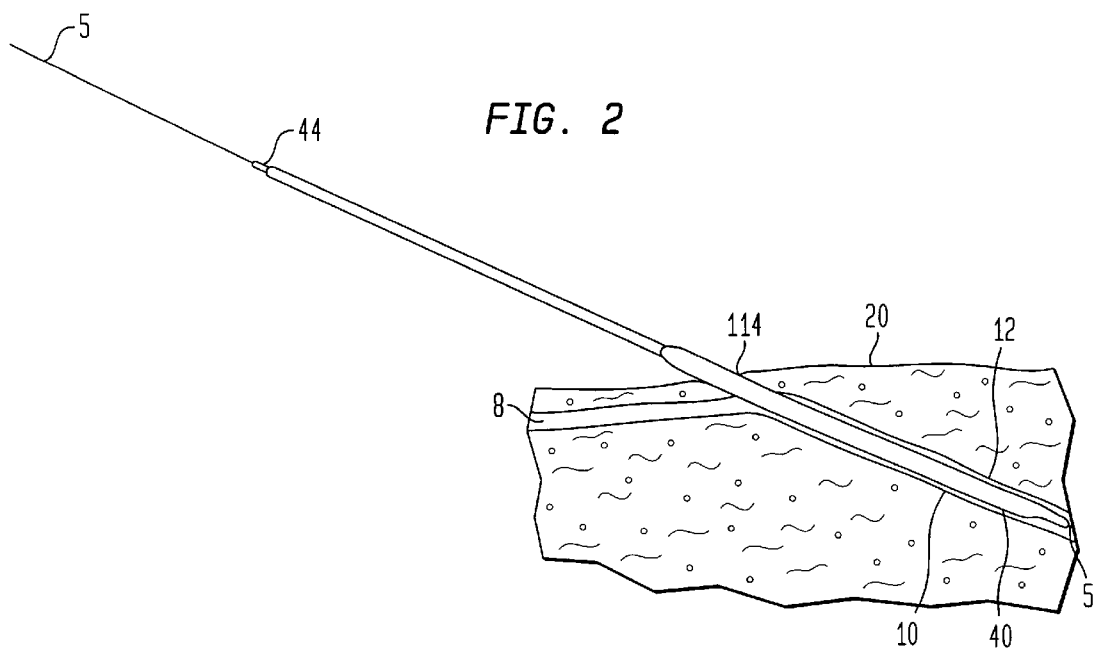
FIG. 2 is a side elevation view of an IAB device showing the IAB bladder being directly inserted into the femoral common artery without an insertion sheath according to the inventive method.
Figure 6:
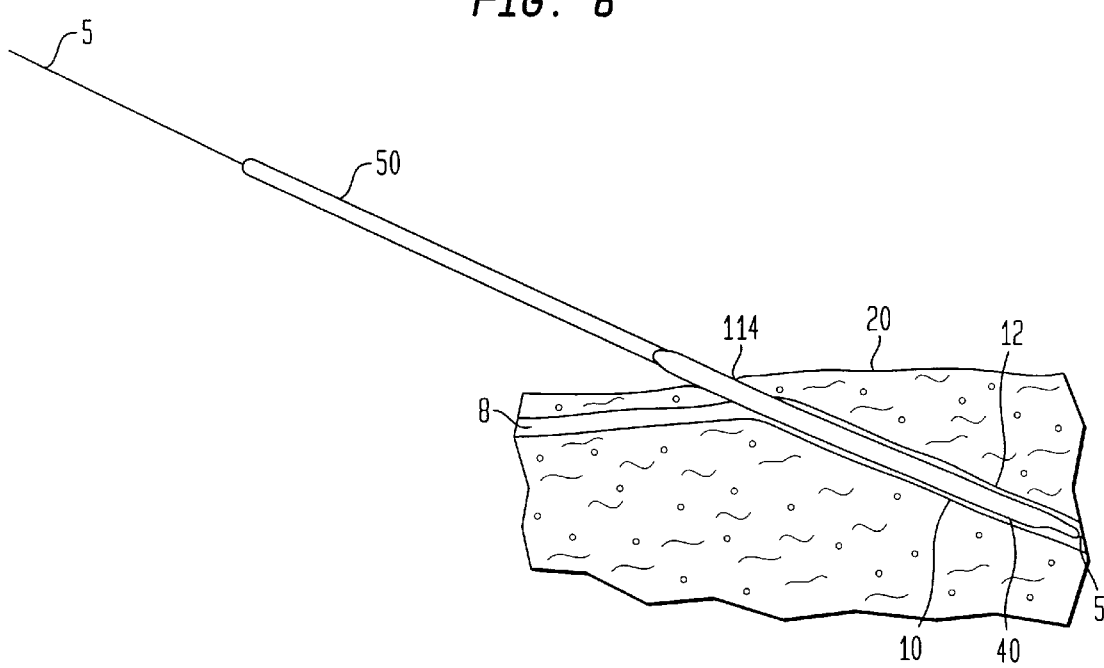
FIG. 6 is a side elevation view of an IAB device showing the IAB bladder connected to an oval catheter of approximately the same cross-sectional area in accordance with the present invention directly inserted into the femoral common artery without an insertion sheath.

With reference to FIGS. 1, 2 and 6 the insertion of an IAB device into the body via a nonsurgical insertion into the femoral common artery through the skin using a percutaneous insertion technique according to the invention will be described. A physician (not shown) would be positioned in the left-hand margin in relation to the various elements being described. In FIGS. 1a–d., 2 and 3, the location of the physician is designated by the symbol "P,". The terms "proximal" and "distal" as used herein shall refer to position relative to that of the physician.

Referring to FIGS. 1 and 2, the IAB device generally comprises IAB bladder 40 which is attached to balloon catheter 42. The IAB is a double lumen device with a central hollow inner lumen 44 and preferably of the type described in U.S. Pat. No. 4,362,150, which patent is incorporated herein by reference. The hollow inner lumen 44 preferably is a hypodermic tubing with a flexible segment within the balloon.

Prior to insertion, the bladder 40 is usually pre-wrapped about itself to reduce its diameter by the manufacturer. The balloon catheter 42 may, for example, as is known in the art is usually connected in a known manner to an intra aortic balloon pumping/monitoring system (also not shown).

The insertion technique according to the invention will now be described.

With reference to FIGS. 1a–d and 3, a small hypodermic needle is inserted through the skin 20 of a patient to perforate or puncture the femoral artery, 10. When blood spurts from the open external end of the needle, placement of the hypodermic needle within the artery 10 is confirmed. A guide wire 5 sufficient in length to reach the central aorta is fed into the artery 10 by passing the guide wire through the center of the hollow hypodermic needle.

Next, the hypodermic needle is removed leaving the guide wire 5 in place. One or more progressively larger dilators is then placed over the guide wire and advanced through the perforated skin 20 and into the artery 10 in order to expand the holds in order to achieve an opening large enough to permit the passage of the wrapped IAB bladder 40. For example, when using a 10.5 French IAB the hole should be dilated to approximately 10 French in diameter. Once the skin 20 and artery 10 have been fully dilated, the dilator is removed and the IAB device is inserted directly into the patient without passing it through the insertion sheath.

Figure 3:
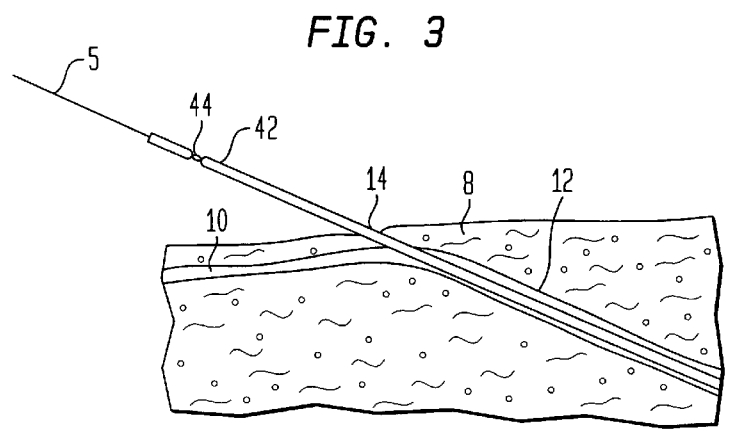
FIG. 3 is a side elevation view of an IAB device showing an oval catheter directly inserted into the femoral common artery without an insertion sheath according to the inventive method.

Referring to FIGS. 1 and 3, the JAB bladder 40 of the prior art even in its wrapped condition has a larger outside diameter than the circular IAB catheter 42. As a result the IAB bladder 40 will dilate the insertion site to a large diameter than that of the catheter 42.

Reference is now made to FIG. 2b which shows from left to right, the circular IAB catheter 42 of FIG. 3 with the IAB bladder 40 now inserted into the aorta (not shown).

As can be seen in FIG. 3, the insertion site 8 after passage of the IAB, may have an opening which due to some inelasticity in the skin was not completely closed around the circular catheter 42, this condition may result in uncontrollable bleeding from the insertion site 8.

As a means to diminish this bleeding when it occurs, the present invention utilizes an oval catheter 50 which is coupled to the IAB bladder 40.

The oval catheter 50 has one of the oval configuration of the type shown in FIG. 4. Oval catheter 50, in the preferred embodiment is only slightly larger than the outside diameter of the normal circular catheter 42 for such an IAB. Preferably, oval catheter 50 has an outside diameter which is about at least as large or slightly larger than the outside diameter of the IAB bladder 40 in its wrapped condition.

FIG. 6 shows the oval IAB catheter 50 now positioned in the insertion site 8 with the insertion site almost completely closed about oval catheter 50.

With reference to FIG. 3, the oval catheter 50 has now been inserted partially into the opening 14 in the wall of the artery 10 with its distal end 52 extending inside the artery 10. The oval catheter 50 is inserted into the artery 10 such that the oval catheter 50, fills the opening 14. As shown in FIG. 6, the oval catheter 50 is thereby able to stops the bleeding which might have resulted after insertion of the normal IAB device. Additionally, the oval catheter 50 dimensioned to pass through the skin 20 and into the artery 10, and is able with its oval configuration to control bleeding without restricting good blood flow through the artery 10 to any great degree.

In accordance with the inventive method, the oval catheter 50 is advanced along the balloon catheter 42 through the skin and into the artery by a sufficient distance to control bleeding from the insertion site 8. In particular, the oval catheter 50 is advanced to a point where its outside oval diameter sufficiently fills the opening made by the passage of the IAB bladder through the skin and artery to provide an elastic contact between the skin opening and the outside diameter of the oval catheter 50. In this previously described insertion two seemingly conflicting requirements are met, namely the cross-sectional area of the catheter 50 is minimized, to allow free flow of blood through the vessel 10 while the perimeter of the catheter 50 is maximized to prevent flow of blood from the insertion site 14. The minimizing of bleeding from the insertion site 14 is the result of the perimeter of the catheter 50 being the same or slightly less than the perimeter of the opening created by the wrapped balloon 40 and therefore chances of bleeding at the insertion site 14 are substantially reduced. Geometrically, this means that the shape of the catheter 50 should not be round. For a given cross-sectional area, a circular body has the minimum cross-sectional area. A non-circular catheter 50 of the same cross-sectional area will have a larger perimeter and will allow for a larger diameter of a wrapped balloon 40. All non-circular designs, shown in FIG. 4 assume the principle of matching the outside cross-sectional area of a 8.5 Fr design catheter 50 while at the same time having an outside perimeter of a 9.0 Fr. catheter. The non-circular designs of FIG. 4 provide a design which allows for adequate inflation/deflation speeds and also accommodate the a regular size of guide wire 5.

Figure 7:
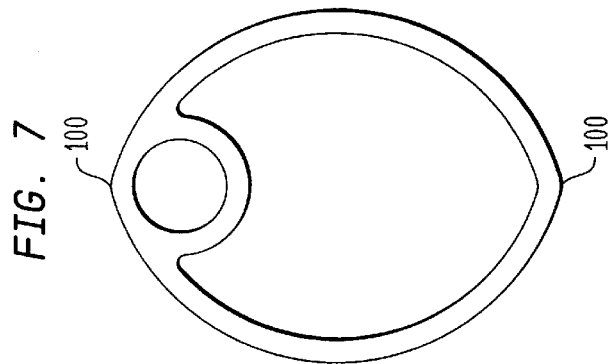
FIG. 7 is an alternative to the oval or non-circular cross-sectional area catheters of FIG. 4, wherein the cross-sectional area is shaped in general the same configuration of the insertion site.

As an alternative to the oval or non-circular catheters of FIG. 4, the catheter may have the shape of FIG. 7. With the catheter having the shape of FIG. 7, it is closer in shape to the insertion site 8 due to the slightly pointed ends 100 of this catheter. These pointed ends 100 match closely the pointed ends 101 of the insertion site 8 and therefore when insertion site 8 has inserted into it the catheter of FIG. 7, insertion site 8 almost completely mates with the catheter of FIG. 7 to form a complete or almost complete seal and therefore substantially prevents blood from leaking from any space that may be between the outer perimeter of catheter of FIG. 7 and the inner perimeter of insertion site 8.

Figure 8:
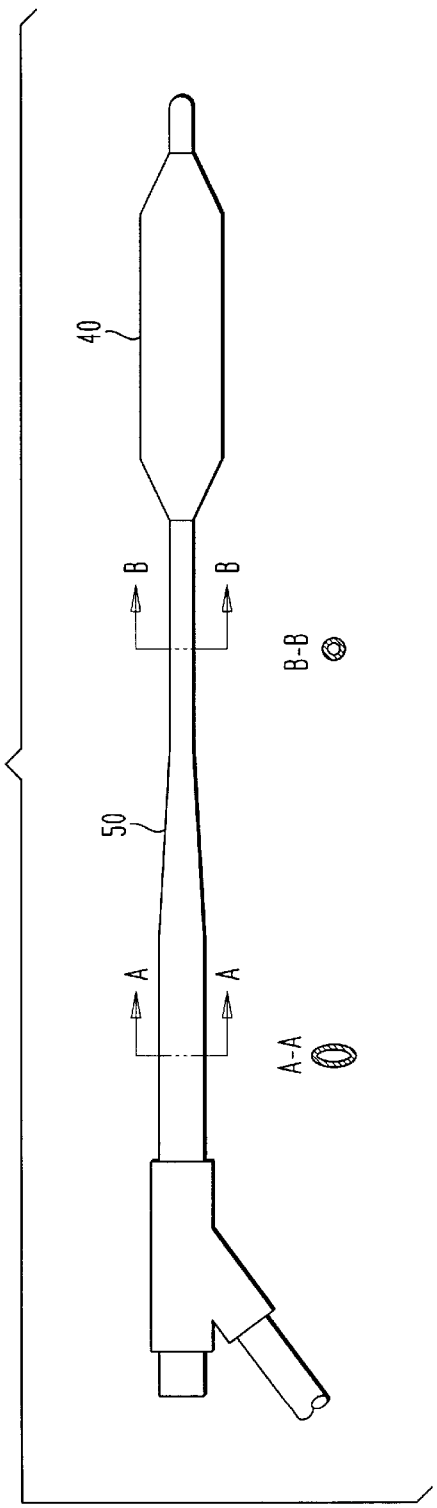
FIG. 8 is a side view of an IAB catheter with circular and non-circular cross-sections.

A further alternative to the catheter 50 is the compound catheter of FIG. 8 in which section A—A is non-circular and section B—B is circular with both section having the same perimeter. In this manner when balloon 40 is tightly wrapped the step down between section B—B and balloon 40 and therefore the size of the insertaion site 8, which is non-circular can also be minimized. But, since section A—A is the section that ultimately contacts the inner perimeter of insertion site 8 when balloon reaches it final location, the non-circular perimeter of section A—A and the non-circular inner perimeter of insertion site 8 substantially match and therefore there is little or no space between the two for blood to leak.

The various features and advantages of the invention are though to be clear form the foregoing description. Various other features and advantages not specifically enumerated will undoubtedly occur to those versed in the are as likewise will many variations and modifications of the invention as defined by the following claims.

We claim:

1. A method for inserting an intra-aortic balloon apparatus through a puncture site in a patient's skin and into the puncture site in a femoral artery, wherein said intra-aortic balloon apparatus includes a tube having a proximal end and distal end, an inflatable and deflateable balloon bladder means sealingly attached at the distal end of the tube and an inner lumen means passing through the length of the intra-aortic balloon apparatus, the method comprising the steps of:

(a) inserting a guide wire into the puncture site in the artery and passing the guide wire up to the patient's aorta;

(b) dilating with dilating means the puncture site to achieve an opening sufficient to permit insertion of the intra-aortic balloon bladder means in a wrapped configuration into the femoral artery;

(c) removing the dilating means;

(d) without the use of an insertion sheath, directly inserting the intra-aortic balloon bladder means in a wrapped configuration over the guide wire and through the puncture site and passing it up to the aorta; and (e) following the balloon bladder with an oval tube, through the insertion site and into the femoral artery to control bleeding from the puncture site by having the puncture site at the femoral artery conform to the oval tube placed in the femoral artery, yet permit blood flow along the femoral artery.

2. The method of claim 1 wherein the oval tube has substantially the dimensions of the perimeter of the balloon bladder means.

3. The method of claim 2 wherein the oval tube is slightly pointed at at least two opposed sides.

* * * * *